PEAR TREE

Filed June 4, 1973 3 Sheets-Sheet 1

United States Patent Office

Plant Pat. 3,599

Patented Aug. 27, 1974

3,599

PEAR TREE

William H. Griggs, Davis, and Ben T. Iwakiri, Sacramento, Calif., assignors to The Regents of the University of California, Berkeley, Calif.

Filed June 4, 1973, Ser. No. 367,048

Int. Cl. A01h 5/03

U.S. Cl. Plt.—36 1 Claim

This invention relates to a new and distinct variety of pear tree to be used primarily as fresh fruit dessert.

For the past twenty years an extensive and continuous pear breeding program has been conducted at the University of California (Department of Pomology) experimental orchards at Davis, Calif. and at the Wolfskill Experimental Orchard near Winters, California. One purpose of the program was to provide improved varieties of pear trees. The present variety of pear tree was the result of endeavors in the conduct of this breeding program.

Figure 1:
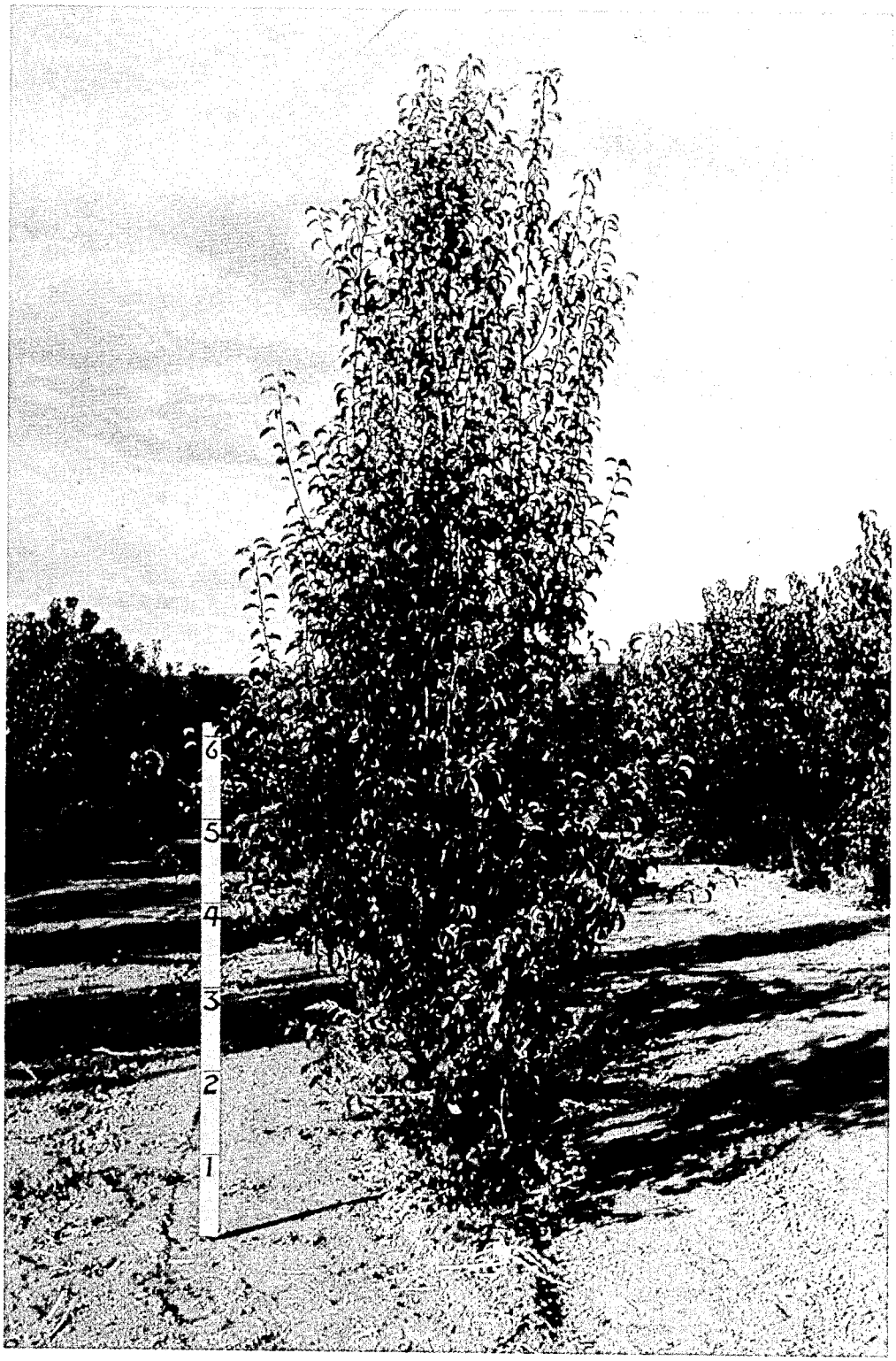
FIG. 1 is a side view of a tree of the new variety at the end of its third growing season.
Figure 2:
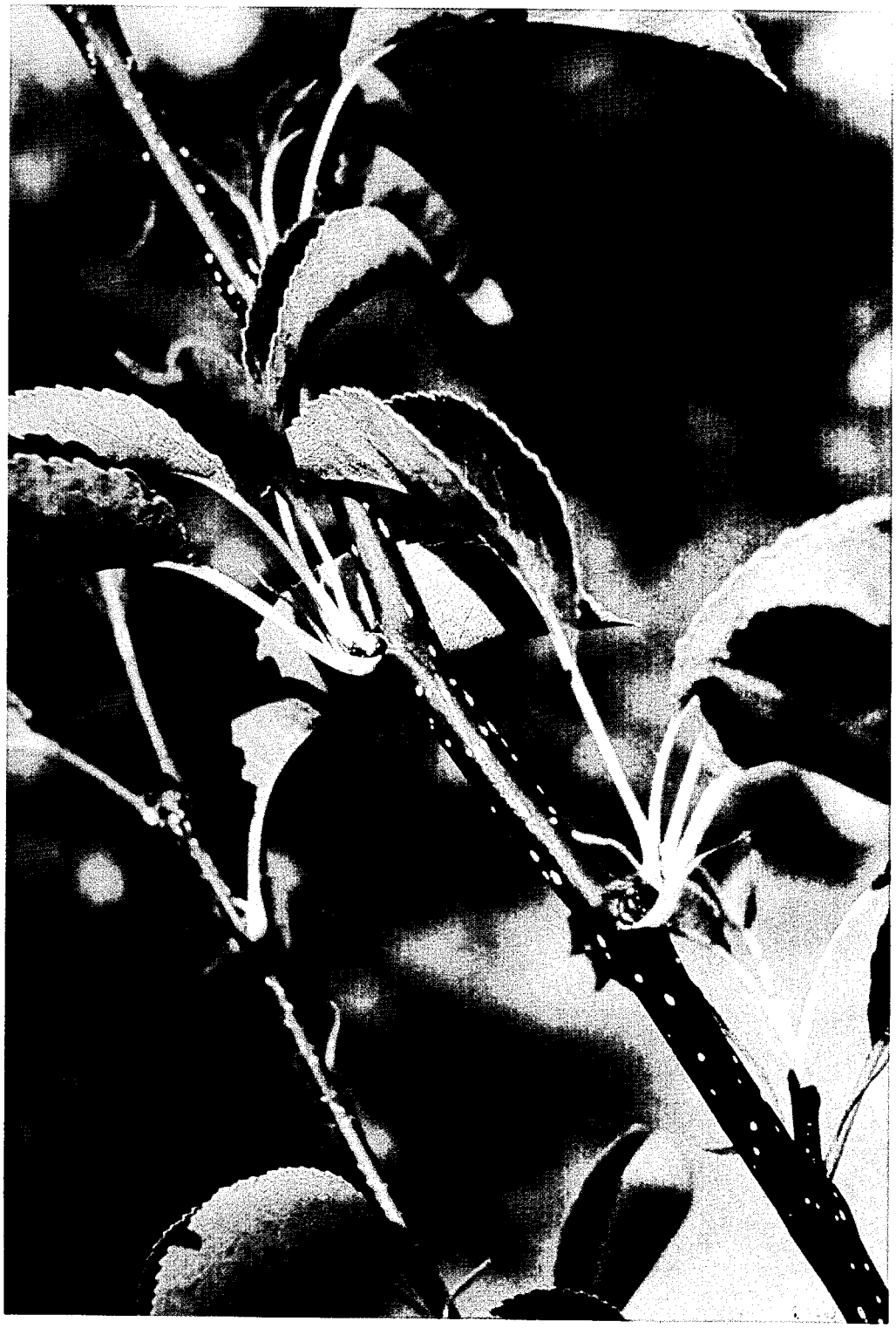
FIG. 2 is a view of a typical branch showing the leaves in folded or bent up position.
Figure 3:
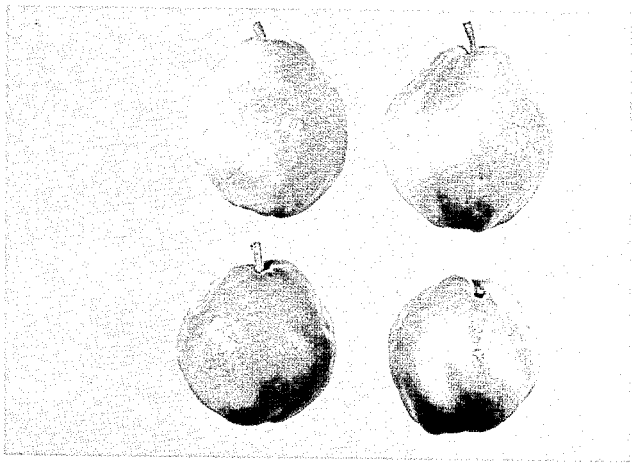
FIG. 3 illustrates fruit of the new variety when in harvest ripe condition.
Figure 4:
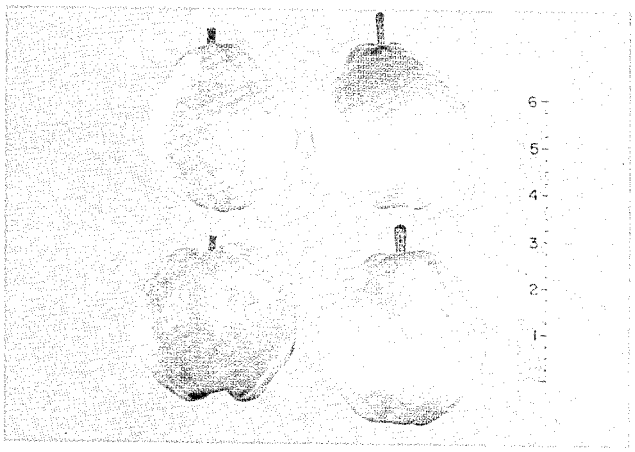
FIG. 4 illustrates fruit of the new variety when in eating ripe condition.
Figure 5:
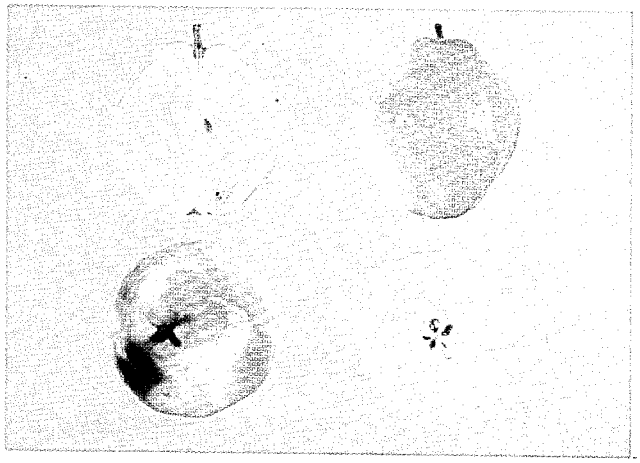
FIG. 5 illustrates fruit of the new variety and its flesh when in eating ripe condition.

The herein disclosed new and distinct variety of pear tree was originated at the University of California (Department of Pomology) experimental orchards at Davis, Calif. in the following manner.

The flowers of a Max-Red Bartlett pear tree (Pat. No. 741 of July 1, 1947) was cross-pollinated with pollen from a Comice (unpatented) pear tree on Apr. 3, 1959. A substantial number of seeds were obtained from the resulting fruit and such seeds were stratified during the winter of 1959–1960 and planted in April 1960. The resultant seedlings were maintained under careful and continuing observation. When such seedlings bore fruit, one—which is the instant variety—evidenced novel and commercially desirable charcteristics and was, therefore, selected for asexual reproduction, preparatory to introduction to the trade.

After its origination, as above, the variety was asexually reproduced by top-grafting on mature *Pyrus communis* pear seedlings in the University of California (Department of Pomology) experimental orchards and by budding into *Pyrus communis* seedlings in the Department of Pomology nursery. The leaves, buds, and fruit resulting from such reproductions all ran true to the parent tree in every respect.

The botanical details of this new and distinct variety of pair tree with color definitions (except those in common color terms), referenced to Maerz, A., and Paul, M. Rea 1930, *A dictionary of color*, McGraw-Hill Book Co., Inc., New York—London, are as follows:

Tree:

*Size.*—Medium to large (similar to Bartlett).

*Vigor.*—Vigorous.

*Growth.*—Upright; spreading; rapid.

*Production.*—Productive.

*Bearing.*—Early; regular bearer.

Trunk:

*Size.*—Medium.

*Texture.*—*Medium* (similar to Bartlett).

Branches:

*Old Growth.*—Size: Medium (similar to Bartlett). Texture: Smooth. Color: Dark brown with dull gray overcast (scarf skin). Lenticels: Numerous; large in size; oblong shape; dark gray in color; relief—raised above surface.

*New Growth.*—Size: Medium (similar to Bartlett). Texture: smooth. Color: Brownish red. Lenticels: Numerous; medium size; some elliptical shape, some diamond-shaped; light tan color; relief—raised above surface.

Leaves:

*Size.*—Leaves from current season's shoots, medium, both length and width. Average length 6.09 centimeters. Average width 3.04 centimeters. Leaves from spurs, medium, both length and width. Average length 5.04 centimeters. Average width 3.00 centimeters.

*Form.*—Oval or obovate. Apices-acuminate. Bases—usually acute, but may be rounded. The leaves are often folded upward from the midrib.

*Thickness.*—Medium, slightly thicker than Bartlett leaves.

*Texture.*—Smooth and leathery.

*Margin.*—Medium serrate to slightly crenate, the serrations are coarser than those of Bartlett.

*Petiole.*—Medium length averaging 2.65 centimeters. Medium thickness averaging 0.8 millimeters.

*Color.*—Top side, Green (Plate 24–L–1); under side, Lighter Green (Plate 21–J–4).

*Venation.*—Pinnate (similar to Bartlett).

Flowers:

*Blooming Period.*—Medium, first bloom 1 to 3 days earlier than Bartlett. Full bloom and last bloom approximately with Bartlett.

*Size.*—Medium (similar to Bartlett).

Fruit:

*Maturity When Described.*—Hard ripe or picking ripe.

*Flesh Firmness.*—15 to 18 pounds (measured with a pressure tester).

*Ripening Period.*—A few days earlier than Bartlett or approximately with Bartlett. The fruits become picking ripe during the first three weeks of August at Davis, Calif.

*Retention.*—Good. Hard ripe fruits are less likely to drop during the preharvest or harvest period than similar fruits of the Bartlett variety.

*Size.*—Large to medium. Average length (well grown specimen), 7.65 centimeters. Average width (well grown specimen), 7.62 centimeters. Fruits are larger than those of Bartlett and similar in size to those of Comice. Uniform.

*Form.*—Longitudinal section, ovate-obtuse-pyriform; ovate or turbinate in some specimens. Transverse section, angular. Uniform. In form this pear resecmbles Comice more than Bartlett.

*Stem.*—Short and thick, average length 1.7 centimeters; average width (near center) 3.9 millimeters. Color, brown (Plate 14–L–8). Lenticels, raised; conspicuous; color, tan; shape, round to elliptical; size, small to medium.

*Cavity.*—Acuminate; deep; angular; sometimes lipped; surface is smooth.

*Basin.*—Deep; broad. Shape, regular. Sides slopping to slightly rounded. Surface is slightly furrowed.

*Calyx.*—Partly open. Lobes separated at the base; partly erect; medium width and length.

Skin:

*Thickness.*—Thin to medium (similar to that of Bartlett).

*Texture.*—Medium (similar to, but somewhat coarser than, that of Bartlett).

*Surface.*—Smooth; generally free of russet; slightly waxy. The blush or exposed areas are glossy. The skin of this pear is not as tender as that of Bartlett and, therefore, is much less subject to ressetting and other blemishes.

*Color.*—Hard ripe or picking ripe fruit—ground color or undercolor, Light green (Plate 21–L–1). Over color, India red (Plate 7–L–6). This dark red color develops on the surface areas exposed to the sun. Surface areas shaded by leaves remain green and give beautiful shadow patterns. Lenticels or dots are light green, medium size (similar to those of Bartlett), numerous, roundish, slightly sunken; conspicuous on red (exposed) surface and inconspicuous on the green ground color. Eating ripe fruit—ground color or undercolor, Yellowish-green (Plate 19–L–2) to yellow (Plate 9–L–4). Over color, Bright red (Plate 5–L–5). Lenticels or dots change from green to yellow and become even more conspicuous in ripe fruit.

The fruit is made strikingly attractive by the bright red overcolor, speckled with yellow dots, in the exposed areas and the contrasting yellow ground color of the shadow areas.

*Flesh (Eating Ripe):*

*Flesh firmness.*—1.5 to 2.5 pounds (measured with a pressure tester).

*Color.*—White (Plate 17–B–1).

*Texture.*—Fine grained; smooth; melting; tender; juicy.

*Soluble Solids (of juice squeezed from the flesh).*—Average 14.8 percent. The juice of this pear is higher in soluble solids than that of Bartlett by approximately 1.5 percent and has about the same percentage soluble solids as that of Comice.

*Flavor.*—Sweet, subacid; refreshing. The flavor is similar to, but slightly milder and less astringent than that of Comice.

*Aroma.*—Aromatic; fragrant; delicate. The characteristic pleasant aroma is more poignant than that of Comice, but not as strong as that of Bartlett.

*Eating quality.*—Excellent.

*Core.*—Small to medium. The core is approximately the same size as that of Bartlett.

*Core Lines (longitudinal section).*—Clasping.

*Calyx Tube.*—Length, medium to short (shorter than that of Bartlett). Width, medium (similar to that of Bartlett). Form (longitudinal section), urn-shaped.

Seed: Medium size; length averages 9.3 millimeters; width averages 5.0 millimeters. Color is Sombrero (Plate 11–D–4). Shape, plump; acuminate.

Use:

*Dessert as Fresh Fruit.*—The bright red blush flowering over the glistening yellows of the shadow areas coupled with the delicious flavor and long shelf life make this pear ideal for the fresh fruit market.

*Season.*—Fall and winter (similar to that of Comice). After three or four weeks in cold storage at approximately 32° F., fruits of this pear will soften to eating ripeness (flesh firmness 1.5 to 2.5 pounds as measured by a pressure tester) in approximately six days at 68° F. to 70° F. Prime quality is obtained when the fruits are removed from cold storage and ripened in late October and November. Good quality may be obtained from fruits held at 31° F. to 32° F. through December.

Keeping Quality: Very good (similar to Comice).

Shipping Quality: Very good (similar to Comice).

The pear tree and its fruit herein described may vary in slight detail due to climatic and soil conditions under which the variety may be grown, the present description being of the variety as grown in the University of California orchards at Davis, Calif.

We claim:

1. The new and distinct variety of pear tree herein described and illustrated and characterized by its medium to large size, rapid vigorous growth and speading shape; said tree coming into bloom one to three days earlier than Bartlett and being an early, regular and productive bearer of medium to large size fruit; said fruit becoming hard or picking ripe approximately the same time as Bartlett and colored a light green ground or under color in its shaded areas and a dark red over color dotted with conspicious green lenticels on its sun exposed areas when ripe; said undercolor becoming yellow and the over color changing to bright red speckled with yellow lenticels while the fruit is ripening; said fruit resembling the fruit of Comice in form, flavor, soluble solids content, season and storage life, but differing therefrom by its poignant aroma, freedom from russet, and highly attractive peach-like beauty imparted by its bright red exposed side contrasted with the glistening yellows of its shaded areas.

No references cited.

ROBERT E. BAGWILL, Primary Examiner